(12) United States Patent
Dakka et al.

(10) Patent No.: US 6,191,308 B1
(45) Date of Patent: *Feb. 20, 2001

(54) PROCESS FOR THE MANUFACTURE OF OXYGENATES

(75) Inventors: Jihad Mohammed Dakka, Kessel-Lo; Georges Marie Karel Mathys, Bierbeek; Hans Karel Theresia Goris, Laakdal, all of (BE)

(73) Assignee: Exxon Chemical Patents Inc., Houston, TX (US)

( * ) Notice: Under 35 U.S.C. 154(b), the term of this patent shall be extended for 0 days.

This patent is subject to a terminal disclaimer.

(21) Appl. No.: 09/171,821

(22) PCT Filed: Apr. 23, 1997

(86) PCT No.: PCT/EP97/02124

§ 371 Date: Aug. 17, 1999

§ 102(e) Date: Aug. 17, 1999

(87) PCT Pub. No.: WO97/41086

PCT Pub. Date: Nov. 6, 1997

(30) Foreign Application Priority Data

Apr. 26, 1996 (EP) .................................................. 96302981

(51) Int. Cl.⁷ .......................... C07C 51/16; C07C 45/27; C07C 47/26
(52) U.S. Cl. .......................... 562/537; 562/589; 568/405; 568/470; 568/475
(58) Field of Search .................................... 568/691, 579, 568/626, 663, 667, 686, 405, 470, 596, 475, 594, 605; 502/77, 78; 549/531; 562/531, 537, 589

(56) References Cited

U.S. PATENT DOCUMENTS

| | | | |
|---|---|---|---|
| 4,891,451 | 1/1990 | Hoelderich et al. | 568/691 |
| 5,025,101 | 6/1991 | Gorun et al. | 556/50 |
| 5,100,852 | 3/1992 | Arntz et al. | 502/77 |
| 5,105,022 | 4/1992 | Holderich et al. | 568/673 |
| 5,354,875 | 10/1994 | Nemeth et al. | 549/531 |
| 5,504,256 | 4/1996 | Bond et al. | 568/575 |

FOREIGN PATENT DOCUMENTS

| | | | |
|---|---|---|---|
| 1003840 | 6/1992 | (BE) . | |
| 2929827 | 2/1981 | (DE) | C07C/43/10 |
| 0100118 | 2/1984 | (EP) | C07C/43/13 |
| 0150280 | 8/1985 | (EP) | C07C/41/50 |
| 0217089 | 4/1987 | (EP) | C07C/43/14 |
| 573334 | 11/1945 | (GB) . | |
| WO9402245 | 2/1994 | (WO) | B01J/29/06 |

OTHER PUBLICATIONS

Synthesis, "Synthesis of χ–Hydroxyacetals" Aug. 1977, pp. 578–579.
Kamitori et al, Tetrahedron Letters, "Alumina as an Versatile Catalyst for the Selective Acetalization of Aldehydes", vol. 26, No. 39, pp. 4767–4770 (1985).
Camblor et al., J. Chem. Soc. Comm., "Synthesis of a Titaniumsilicoaluminate Isomorphous to Zeolite Beta and its Application as a Catalyst for the Selective Oxidation of Large Organic Molecules", No. 8, pp. 589–590 (1992).
Corma et al., J. Chem. Soc. Comm., "Synthesis of an Ultralarge Pore Titanium Silicate Isomorphous to MCM–41 and its Application as a Catalyst for Selective Oxidation of Hydrocarbons", pp. 147–148 (1994).
J. Chem. Soc. Chem. Comm., "Localized Basification of Catalytic Surfaces enhances the Selective Oxidation of L–Sorbose over Supported Pt Catalysts modified with Tertiary Amines", pp. 1377–1378 (1995).
Chemische Berichte, vol. 41, pp. 3599–3612. (1908).

*Primary Examiner*—Sreeni Padmanabhan
(74) *Attorney, Agent, or Firm*—Douglas J. Collins

(57) ABSTRACT

α-Hydroxycarbonyl compounds are obtained from aldehydes or ketones by forming an acetal or ketal which is decomposed to a vinyl ether. The ether is selectively oxidized under conditions yielding an α-hydroxy-aldehyde or α-hydroxy-ketone with the carbonyl group protected. The last-mentioned compounds are valuable sources for other functional organic molecules, for example lactic acid.

25 Claims, No Drawings

PROCESS FOR THE MANUFACTURE OF OXYGENATES

This Application is the U.S. National Stage Application of PCT/EP97/02124 filed Apr. 23, 1997.

This invention relates to processes for the manufacture of organic compounds, and more especially to the manufacture of oxygenates of hydrocarbons.

In the industrial preparation of functional organic compounds, it is desirable that a given reaction proceeds in good yield and high specificity. There are numerous routes to organic molecules containing a hydroxy group. The yield resulting from a number of such routes is, however, not high, and environmentally acceptable effluent disposal and separation of the product from by-products add to costs.

The need for an improvement in manufacturing processes is exemplified by lactic acid production.

Lactic acid, 2-hydroxypropionic acid, and its derivatives, especially salts and esters, have many industrial uses, primarily in the food industry but also increasingly in the manufacture of biodegradable polymers. Much of the product has long been obtained by fermentation of hexoses or hexose-producing raw materials, a procedure from which much unwanted by-product and effluent result; known synthetic methods, for example using acetaldehyde, propene, or propionic acid, as starting materials, have grown in commercial importance but they too present some environmental problems, and yields admit of improvement.

As discussed in Chemistry in Britain, December 1996, 45, the lactic acid produced by fermentation is neutralized as it is produced by calcium carbonate and, to keep the salt in solution so that it may be separated from residues by filtration, its concentration has to be kept low, resulting in high plant capacity requirements and hence costs. The workup, including carbon treatment, evaporation and sulphuric acid treatment, produces stoichiometric quantities of calcium sulphate, and the resulting lactic acid is only of technical grade. Purification entails esterification, distillation and hydrolysis, with their associated waste production. If chemical synthesis is used, acetaldehyde is treated with HCN to give lactonitrile, which is hydrolysed using sulphuric acid resulting in the low value product ammonium sulphate. Again, for purification, the crude acid has to be esterified and the ester hydrolysed. Both commercial procedures are therefore costly in energy and, inter alia, waste disposal.

There are also numerous synthetic routes by which a hydroxy group may be introduced into a ketone. For example, hydroxyacetone, a molecule with numerous uses as an intermediate in food, fine chemicals and pharmaceutical preparation and elsewhere, for example, as a solvent, is typically made by bromination of acetone and nucleophilic replacement of the bromine substituent by a hydroxy group. Environmentally acceptable effluent disposal and separation of the desired product from by-products (which here include the aldol condensate typically resulting in the alkaline environment prevailing) again add to costs.

There clearly remains a need for a better synthetic route to many hydroxy-substituted carbonyl compounds.

In "Zeolites: A Refined Tool for Designing Catalytic Sites", edited by Bonneviot and Kaliaguine (Elsevier, 1995) Yang and Wang describe the elimination of methanol from dimethylacetal, forming methyl vinyl ether, over aluminophosphate molecular sieves and zeolites.

In Synthesis, August 1977, p 578, Frimer describes the preparation of an α-hydroxy acetal by peracid epoxidation of the corresponding enol ether in an alcoholic solvent.

In U.S. Pat. No. 5,354,875 there is disclosed the epoxidation of olefins, including vinyl ethers, using a mixture of titanium silicalite and titania.

In this specification, the term "vinyl ether" is used to denote a compound in which one of two carbon atoms joined by an olefinic bond is linked to the ether oxygen.

The present invention provides a process for the manufacture of an α-hydroxy aldehyde or ketone in which the carbonyl group is protected which comprises (a) forming an acetal or ketal by reaction of an aldehyde or ketone and an alcohol or an ortho-ester, (b) decomposing the acetal or ketal to form a vinyl ether, and (c) oxidizing the vinyl ether in the presence of a carbonyl group-protective reagent to form the α-hydroxy aldehyde or ketone with the carbonyl group protected.

The reaction, step (a), between the aldehyde or ketone and the alcohol is desirably carried out with the alcohol in molar excess, advantageously in at least twice molar proportions for a monohydroxy alcohol, preferably in a molar proportion of aldehyde:alcohol within the range of from 1:2 to 1:10 and more preferably from 1:2 to 1:6. Although not at present preferred, a dihydroxy alcohol may be used, in which case equimolar proportions suffice. While an elevated temperature facilitates rapid reaction and good conversion, any temperature within the range of from room temperature to 120° C., preferably about 100° C., may be used, advantageously at autogenous pressure.

As aldehyde, there may be mentioned, more especially, an aliphatic aldehyde, for example, acetaldehyde, propanal, a butanal, a pentanal or a hexanal, or an araliphatic aldehyde, e.g., phenylacetaldehyde. As ketone, there may be mentioned, more especially, an aromatic ketone, for example, acetophenone.

As the alcohol there may be mentioned more especially aliphatic alcohols, preferably saturated aliphatic alcohols, for example, methanol, ethanol, 1-propanol, as monohydroxy alcohols, and ethylene glycol as a dihydroxy alcohol. Alcohols having more than two hydroxy groups may be used, but are not at present preferred.

For ketal formation, the use of an ortho-ester is preferred to the use of an alcohol, e.g., ethyl orthoformate, $CH(OC_2H_5)_3$ may be used with good results.

The formation of the acetal or ketal is desirably carried out in the presence of a metallic halide, e.g., an alkaline earth halide, e.g., calcium chloride, or an acid catalyst, either heterogeneous or homogeneous e.g., a mineral acid, a Lewis acid, or a molecular sieve in acid form. Advantageously, a heterogeneous catalyst is used; as examples there may be mentioned a molecular sieve, for example, a silicon aluminophosphate, e.g., SAPO-5, 11 or 34, or, preferably, a zeolite, e.g., H-β, HMCM-41, H-Mordenite, H-Faujasite, or H-ZSM-5. A molecular sieve of the higher acidity represented by the zeolite examples is preferred, as is one that, like the zeolites, is relatively hydrophobic.

The molecular sieve may be used on a support, e.g., of silica or alumina, and dry silica gel and alumina may themselves be active catalysts in this reaction, as described by Kamitori, et al, Tetrahedron Letters, 26, 39, 4767 (1985).

The reaction may be carried out at room temperature or, preferably, an elevated temperature, advantageously of at least 80° C., preferably at least 100° C., in the liquid or gaseous phase, the liquid phase reaction being preferred, giving high conversion and selectivity.

The resulting acetal or ketal may readily be decomposed, step (b), by elimination of one molecule of alcohol to form a vinyl ether or by ring opening if the acetal is formed by a dihydric alcohol. Decomposition may be effected by pyrolysis, for example, by heating in an inert atmosphere at a temperature within the range of from 150 to 500° C., more especially from 250 to 400° C. A WHSV within the range of from 0.1 to 100, if desired or required using a catalyst, may conveniently be used. As catalysts there may be mentioned a supported noble metal catalyst, e.g., silver or platinum on silica or alumina, an acid catalyst, e.g., phosphorus pentoxide or p-tosyl acid, or, preferably, a molecular sieve catalyst. As molecular sieve, a weakly acid, medium or small pore material is preferred, e.g., Na-Mordenite, SAPO-34 and AlPO$_4$-11. U.S. Pat. Nos. 4,891,451, 5,100,852, and 5,105,022, the disclosures of which are incorporated herein by reference, propose various catalysts (e.g., Mordenite, ZSM-5, borosilicate and iron silicate zeolites, and phosphate molecular sieves) for a reaction of this type.

If desired, steps (a) and (b) may be combined, in a process in which an aldehyde or ketone and an alcohol are reacted under conditions in which a vinyl ether results. While not wishing to be bound by any theory, it is believed that an acetal or ketal resulting from an initial reaction is decomposed by an elimination reaction to yield the ether. In any event, any intermediate, whatever its nature, need not be isolated. Advantageously, to effect direct vinyl ether formation, the reaction may be carried out at a temperature within the range of 200° C. to 400° C. Advantageously, a molar ratio of alcohol:aldehyde or ketone within the range of from 2:1 to 16:1 is employed. Advantageously, a catalyst as described above with reference to step (a) or step (b), and preferably with reference to step (a) is employed.

As indicated above, reaction of the vinyl ether, to introduce a hydroxy group on the carbon atom of the double bond remote from the ether oxygen, step (c), is effected in the presence of an oxidizing agent and a compound that forms a bond with the carbon atom linked to the ether oxygen and provides a proton to the molecule. Such a protic masking or protecting compound may be, for example, an acid, especially a carboxylic acid, an amine, a thiol, or, advantageously, an alcohol, in which case the resulting product is an α-hydroxy acetal or ketal.

The alcohol is advantageously a low-boiling alcohol, e.g., ethanol, methanol or n-propanol. The alcohol is advantageously present in at least a stoichiometric quantity, advantageously in a molar ratio of at least 5:1, preferably at least 10:1, and most preferably at least 40:1. The reaction may be carried out in solution, in which case an excess of alcohol reactant may conveniently act as solvent.

Oxidation of the vinyl ether in the presence of an alcohol to form an α-hydroxy acetal or ketal may employ the same alcohol as in the formation of the initial acetal, or a different alcohol. As oxidizing agent, which may if desired be generated in situ, there may be mentioned, for example, a peroxy acid, e.g., a perbenzoic acid such, for example, as a chloroperbenzoic acid, perpropionic acid, hydrogen peroxide, or an organic hydroperoxide, for example tert-butyl hydroperoxide (TBHP). Alternatively, an inorganic oxidant may be used. Examples include persulphates and hypochlorites.

Advantageously, an oxidation catalyst is employed, either a homogeneous or, preferably, a heterogeneous catalyst being suitable, for example, a metal oxide deposited on an amorphous support, e.g., silica, or a metal aerogel or xerogel. A heteropolyanionic acid catalyst is also suitable, for example, a polyoxometallate of the general formula $XM_{12}O_{40}^{x-8}$ wherein M represents a metal ion, e.g., Mo(VI), W(VI) or V(V), X represents P(V) or Si(IV) and x represents the oxidation state of the atom X. (See Cat. Rev. Sci. Eng. (1995) 37(2), 311 to 352).

Another suitable catalyst is a tetranuclear manganese complex or a tetranuclear metal complex having a mixed metal core, as described in U.S. Pat. Nos. 5,025,101 and 5,504,256, the disclosures of which are incorporated herein by reference. Preferably, a transition metal oxide catalyst in a high oxidation state, e.g., Mo(VI), W(VI), Ti(IV), Cr(VI), Zr(IV), V(V), Os(VI), Se(IV), Re(IV, VI, and VII) and Ru(VI and VIII), or a molecular sieve, especially a metal-containing, more especially a titanium-containing, molecular sieve, especially one in which at least part of the metal forms part of the structure of the molecular sieve, is used. Most preferably a Ti-silicalite, e.g., TiMCM-41, TS-1, or TS-2, or TiSAPO or TiAPO, or a zeolite, e.g., Ti-β, is used. Advantageously, the molecular sieve contains an alkali metal or other small radius cation, e.g., K, Na, or, preferably, Li. Reaction conditions vary with the catalyst and oxidant. A temperature in the range of room temperature to 150° C., preferably 40° C. to 100° C., at reaction times of from 30 minutes, especially 1 hour, to 10 hours, may typically be used.

The invention also provides processes in which the product of step (c), the protected aldehyde or ketone, is further treated to yield other valuable types of molecules.

Among these, there may more especially be mentioned processes in which:

(d) the protected aldehyde or ketone is hydrolysed to the corresponding unprotected α-hydroxy aldehyde or ketone;

(e) the protected aldehyde is hydrolysed to the corresponding unprotected aldehyde and in a second step (f) is oxidized to an α-hydroxy acid, (g) the protected aldehyde is hydrolysed and oxidized in a single step to an α-hydroxy acid.

(h) the protected aldehyde is oxidized to an α-aldehydic (α-formyl) acid, (j) the protected aldehyde is hydrolysed and rearranged to an α-hydroxy ketone, (k) the protected aldehyde is oxidized to an α-keto (α-oxo) acetal, which is optionally, (l) hydrolysed to an α-keto (α-oxo) aldehyde, which is optionally, (m) oxidized to an α-keto (α-oxo) acid.

The protected α-hydroxyaldehyde or ketone may be hydrolysed, step (d), if desired in situ, by a number of different routes. For example, acid hydrolysis provides an α-hydroxyaldehyde or ketone, using a dilute mineral acid or an ion exchange resin or a molecular sieve in acid form. Hydrolysis using dilute sulphuric acid is described by A. Wohl, Berichte, 1908, 3599 at 3608, using 0.1 N sulphuric acid for 3 days at room temperature.

At a given temperature, overall conversion is enhanced as the mole ratio of water to hydroxyacetal is increased to about 20:1, as is the molar proportion of 2-hydroxyaldehyde formed. Advantageous molar ratios are in the range of 5:1 to 20:1. Since the competing reaction (i) isomerization of the hydroxyaldehyde to a hydroxyketone, takes place under hydrolysis conditions, reaction times are advantageously limited as much as is consistent with good conversion if the aldehyde is required.

Overall conversion increases with catalyst concentration, as does the rate of isomerization to hydroxyketone. Accordingly, moderate catalyst concentrations, e.g., up to 5 wt %, based on acetal, are used if the aldehyde is required.

While higher temperatures, e.g., up to 90° C., improve conversion, they also favour hydroxyketone yield, and a temperature up to 70° C. is preferred if the aldehyde is required.

If recovery of the α-hydroxy aldehyde is required, this may be effected by distillation or solvent extraction. Alternatively, the reaction mixture may be oxidized without separation of the aldehyde, the latter being selectively oxidized.

The now unprotected aldehyde may be oxidized, step (f), e.g., by molecular oxygen, air, or a hydroperoxide. The oxidation may be carried out in the presence of a catalyst, e.g., a supported noble metal (for example, silver, palladium or platinum), catalyst.

Alternatively, the protected α-hydroxyaldehyde may be hydrolysed and oxidized in a single step (g), to an α-hydroxy acid. This may in turn be dehydrated to yield an α-olefinic acid, or esterified, or reacted to form a salt or an amide. The α-hydroxy acid is advantageously lactic acid. In a preferred embodiment of the invention as represented by processes in which steps (e) and (f) are, or step (g) is, carried out, the invention provides a process for the manufacture of lactic acid which comprises forming an acetal by reaction of propanal and an alcohol, decomposing the acetal to form a propene ether, oxidizing the ether in the presence of an aldehyde group-protecting reagent to yield a protected 2-hydroxypropanal and removing the protection from the aldehyde group and oxidizing the resulting 2-hydroxypropanal to form lactic acid.

It will be appreciated that this reaction sequence corresponds to steps (a) to (d) and either (e) and (f) or (g) or the general reaction sequence above, and that the reactions and conditions exemplified for the general reaction are suitable or preferred for the manufacture of lactic acid.

As indicated above, lactic acid is a valuable product itself, and may be used in the manufacture of valuable low-toxicity solvents for example by esterification. Examples of lactic acid esters are the methyl, ethyl and linear and branched $C_3$ to $C_8$ alkyl esters, especially isopropyl, n-butyl, and 2-ethylhexyl esters. There may also be used as esterifying alcohols the commercially available Exxal (trade mark) alcohols, which are mixtures of mainly branched alkanols, with, e.g., 7 to 13 carbon atoms.

The processes according to the invention may be carried out with good yields and selectivity to the desired products, with the various protective materials being recyclable.

If the protected α-hydroxyaldehyde, especially the 2-hydroxyacetal, is oxidized without hydrolysis, an α-aldehydic acid may be formed.

Step (j), the hydrolysis and rearrangement of a protected aldehyde to an α-hydroxyketone is a valuable process per se. The present invention accordingly also provides a process for the manufacture of an α-hydroxyketone which comprises hydrolysing an α-hydroxyaldehyde in which the carbonyl group is protected and rearranging (isomerizing) the resulting α-hydroxyaldehyde to an α-hydroxyketone, the process being carried out in the presence of an acid catalyst. In this aspect of the invention, the α-hydroxyaldehyde may be an aliphatic or araliphatic aldehyde, for example, glycolaldehyde, an α-hydroxy substituted propanal or, linear or branched, butanal, pentanal or hexanal. As indicated above, the aldehyde group may be protected by, for example, an acid, especially a carboxylic acid, an amine, a thiol or, advantageously, an alcohol, in which case the protected molecule is an acetal, to which reference will hereinafter be made for simplicity. As protecting alcohol there is advantageously employed a low-boiling alcohol, for example methanol, ethanol, or n-propanol.

As examples of suitable acid catalysts there may be mentioned inorganic or organic acids, ion exchange resins and molecular sieves. Homogeneous or heterogeneous catalysts may be used. As inorganic acid catalysts, for example, there may be mentioned sulphuric, hydrochloric acid, including Lewis acids, while as organic acid there may be mentioned for example, acetic acid.

As molecular sieve there may be mentioned, for example, a silicon aluminophosphate, e.g., SAPO-5, 11 or 34, or, preferably, a zeolite, e.g., H-β, H-Mordenite, H-Faujasite, or H-ZSM-5. A molecular sieve of the higher acidity represented by the zeolite examples is preferred, as is one that, like the zeolites, is relatively hydrophobic.

The molecular sieve may be used on a support, e.g., of silica or alumina.

As indicated above with reference to reaction (d), at a given temperature, although the hydrolysis reaction is enhanced as the mole ratio of water to hydroxyacetal is increased to about 20:1, the rearrangement (isomerization) is inhibited, resulting in a lower proportion of α-hydroxyketone compared with remaining α-hydroxyaldehyde. Advantageous molar ratios are therefore in the range of 1:1 to 10:1 if the hydroxyketone is required. The longer the reaction time, the greater the extent of isomerization from α-hydroxyaldehyde to α-hydroxyketone.

An acetal:catalyst ratio in the range of from 1:1 to 1000 to 1 by weight may conveniently be used. The rate of isomerization to hydroxyketone increases with catalyst concentration. Accordingly, relatively high catalyst concentrations, e.g., in the range of from 10 to 20 wt %, based on acetal, are in this case preferred.

The process of this aspect of the invention may be carried out in the liquid or the gaseous phase. Higher temperatures, e.g., up to 100° C., improve conversion, and also favour hydroxyketone yield, and a temperature in the range of from 70° C. to 90° C. is preferred.

Recovery of the desired α-hydroxyketone from unreacted starting materials and α-hydroxyaldehyde may be effected by, for example, distillation or solvent extraction.

As an example of steps (k) to (m) above, oxidation of an α-hydroxyacetal to an α-ketoacetal, its hydrolysis to an α-ketoaldehyde, and its oxidation to an α-keto acid, there may be mentioned the transformation of 2-hydroxy-1,1-dimethoxypropane to pyruvic acid.

An aldehyde required as starting material for the aldehyde-related processes of the invention may readily be produced by hydroformylation of an olefin, if desired in a dilute feedstream.

The following Examples illustrate the invention:

Step (a)—Acetal Formation

EXAMPLE 1

Methanol (2.0 moles) and anhydrous calcium chloride (0.16 mole) were mixed in a glass vessel under nitrogen. An exotherm took the temperature to about 40° C., and the vessel was placed in an ice bath to cool it to about 4° C. Propanal (1.0 mole) at 4° C. was slowly added with continued cooling, the reaction mixture being stirred and cooled for 24 hours. GC, IR, and NMR analysis showed an 86.7% conversion and 100% selectivity to 1,1-dimethoxypropane.

EXAMPLES 2 to 7

These examples employed acid molecular sieves as catalysts. Propanal and methanol were mixed at a molar ratio of 1:8. In each Example, 20 g of reaction mixture were employed together with 0.15 g of catalyst. The reaction mixture was heated in a closed vessel to 100° C. and maintained at that temperature for 1 hour. The acetal 1,1- dimethoxypropane was purified by distillation. Analysis as in Example 1 indicated the conversion of propanal and selectivities achieved; Table 1 gives the results.

TABLE 1

| Example | Catalyst | Conversion % | Selectivity % |
|---------|----------|--------------|---------------|
| 2 | H-β | 92 | 100 |
| 3 | HMCM-41 | 87 | 100 |
| 4 | H-ZSM-5 | 91 | 100 |
| 5 | SAPO-5 | 79 | 100 |
| 6 | SAPO-11 | 77 | 100 |
| 7 | SAPO-34 | 80 | 100 |

EXAMPLES 8 to 11

Part of a 60 cm long tubular reactor, diameter 18 mm, was filled with 3.3 mm diameter glass beads and the remainder, 20 cm, with a mixture of the glass beads and catalyst. The catalyst was prepared by pelletizing a 30% H-β zeolite and 70% (by weight) gamma-alumina binder mixture, calcining the pellets at 550° C. for 10 to 16 hours, crushing, and using the fraction between 1 and 2 mm. The reactor was placed in a tubular oven and heated at the temperatures indicated in Table 2 below. A reaction mixture of propanal:methanol at a molar ratio 1:16.4 is passed through the reactor at 1 ml/minute in admixture with argon at the rate shown.

TABLE 2

| Ex. No. | Temperature ° C. | Argon Gas Flow ml/min. | Conversion % | Selectivity, % | |
|---------|------------------|------------------------|--------------|----------------|---|
| | | | | to Acetal | to Ether |
| 8 | 200 | 10 | 27.2 | 52 | 13.8 |
| 9 | 300 | 10 | 43.4 | 1.9 | 21.9 |
| 10 | 150 | 5 | 45.2 | 100 | 0 |
| 11 | 150 | 10 | 51.7 | 86.6 | 0 |

Examples 8 and 9 illustrate that if desired steps (a) and (b) may be combined.

Step (b)—Preparation of Propenyl Ether

EXAMPLES 12 and 13

A tubular reactor, of diameter 18 mm and length 50 cm, was filled with 185 g of 3 mm glass beads, and heated in a tubular oven to the temperatures shown in Table 3. 1,1-dimethoxypropane was fed to the oven at 1 ml/minute together with 10 ml/minute argon, an HSV of 0.27 l/h. The conversion and selectivity to 1-methoxypropene are given in Table 3.

TABLE 3

| | Example 12 | Example 13 |
|---|------------|------------|
| Reaction Temperature, ° C. | 300 | 400 |
| Selectivity to propenyl ether, % | 100 | 100 |
| Conversion, % | 26 | 86 |
| Cis:Trans Ratio | 1:2 | 1:2 |

Step (c)—Oxidation to α-hydroxyacetal

EXAMPLE 14

10 g (0.3 mol) of methanol were mixed with 7 mmol of 1-methoxy propene and cooled to 8° C. 7 mmol of 3-chloroperoxybenzoic acid were added over 40 minutes with continued cooling, and then the temperature was increased to room temperature and maintained for 30 minutes. GC and NMR analysis showed 100% conversion, of which 70.6 mol % was to 2-hydroxy-1,1-dimethoxypropane (hydroxyacetal) and 29.4 mol % was to 1,1-dimethoxypropane.

EXAMPLE 15

5 g (0.16 mol) of methanol were mixed with 5 mmol $H_2O_2$ (30% in $H_2O$) and 20 mmol of 1-methoxypropene. 0.25 g of TS-1 were added, and the mixture heated at 40° C. for 2 hours. Analysis showed 98% conversion of $H_2O_2$ and 46% conversion of the methoxypropene, of which 54 mol % was to 2-hydroxy-1,1-dimethoxypropane and 46 mol % was to 1,1-dimethoxypropane.

EXAMPLE 16

5 g (0.16 mol) of methanol were mixed with 14 mmol of 1-methoxypropene and 14 mmol of TBHP (80% in di-tert butylperoxide). 0.1 g TiMCM-41 were added and the mixture heated at 100° C. for 1 hour. 99% of both the methoxypropene and the TBHP were converted; the molar selectivity was 56% to hydroxyacetal, 38% to 1,1-dimethoxypropane and 8% to 1-methoxy-1-perbutoxypropane.

EXAMPLE 17

10 g (0.3 mol) of methanol were mixed with 10 mmol of TBHP (80% in di-tert butyl peroxide) and 40 mmol of 1-methoxypropene. 1 mmol of $Mo(CO)_6$ was added, and the mixture heated at 50° C. for 3 hours. The conversion of TBHP was 100%, and that of 1-methoxypropene was 61.5%, of which the molar selectivity was 41.5% to α-hydroxyacetal and 58.5% to 1,1-dimethoxypropane. The efficiency of the TBHP was 100%.

EXAMPLES 18 to 23

In these examples, the effect on vinyl ether oxidation (step c) of ion-exchanging the acid form of the Ti-containing catalyst with a cation of small ionic radius was examined. Ion-exchange was effected using a 1% by weight lithium acetate solution, 0.5 g of catalyst in the acid form being added to 10 ml of solution. The resulting slurry was heated to 80° C. and maintained at that temperature for 30 minutes with stirring. After cooling to room temperature, the slurry was centrifuged at 12,000 r.p.m. Treatment of the catalyst was repeated twice, and the resulting product washed with water at 80° C. three times and then with methanol at 40° C. three times. The catalyst was dried at 120° C. and calcined at 500° C. Four catalysts were treated in this way.

Catalyst 1—Tiβ made by the procedure of International Application WO 94/02245. 1H is original (hydrogen) form, 1Li is lithium form.

Catalyst 2—Tiβ made generally by the procedure of J. Chem. Comm. 1992, 589. 2H is original form, 2Li is lithium form.

Catalyst 3—TiMCM-41 made by the procedure of J. Chem. Soc. Chem. Comm. 1994 (A. Corma et al). 3Li is lithium form.

Catalyst 4—TS-1. 4Li is lithium form.

In each case, 5 g (0.16 mol) of methanol were mixed with 5 mmol of $H_2O_2$ (30% in $H_2O$) and 20 mmol of 1-methoxypropene. 0.25 g of catalyst were added, and the mixture heated at 40° C. for 40 minutes. Table 4 below summarizes the results.

TABLE 4

| Ex. | Catalyst | Conv, % | Efficiency, % | Ether Conv, % | Selectivity to HO-acetal | Acetal |
|---|---|---|---|---|---|---|
| 18 | 1H | 33 | 91 | 100 | 7.5 | 92.5 |
| 19 | 1Li | 97 | 82 | 86.4 | 23 | 77 |
| 20 | 2H | 15 | 98 | 100 | 3.6 | 96.4 |
| 21 | 2Li | 100 | 100 | 75 | 34 | 66 |
| 22 | 3Li | 100 | 100 | 83.3 | 30 | 70 |
| 23 | 4Li | 100 | 100 | 28.2 | 88 | 12 |

In the table above, "Conv." indicates the percentage of $H_2O_2$ added that is consumed, while "Efficiency" indicates the percentage of that consumed which is used in formation of the desired product.

Step (d)—Hydrolysis of Hydroxyacetal and Oxidation to Lactic Acid—2 stage—Examples 24 to 30
Part 1—Hydrolysis;

EXAMPLES 24 to 29

2 g of 2-hydroxy-1,1-dimethoxypropane were mixed with 20 g of water in the presence of an acid catalyst. In Example 24, the temperature was maintained at room temperature for 5 days, while in Examples 25 to 29 the reaction mixture was maintained at 60° C. for 5 hours. Table 5 below indicates the catalyst, catalyst strength, reaction and conversion in each case.

TABLE 5

| Example No. | Acid | $H^+$/Acetal (molar) | $H^+$ conc (mol/l) | Conv. % |
|---|---|---|---|---|
| 24 | $H_2SO_4$ | 1/33 | 0.05 | 100 |
| 25 | $H_2SO_4$ | 1/500 | 0.00075 | 100 |
| 26 | $H_2SO_4$ | 1/250 | 0.00150 | 99 |
| 27 | $H_2SO_4$ | 1/100 | 0.00375 | 100 |
| 28 | Amberlyst 15 | — | 4 g/l | 99 |
| 29 | Zeolite HB | — | 50 g/l | 100 |

"Amberlyst" is a trade mark for an ion exchange resin.

EXAMPLE 30

Hydroxypropanal was oxidized with oxygen at atmospheric pressure in a 50 ml flask equipped with a stirrer, condenser and port for gas inlet. Hydroxypropanal solution (2 g in 20 ml water) and a 5% platinum on carbon catalyst (0.1 g) were loaded into the flask with stirring at 60° C. Oxygen was bubbled for 5 hours, the oxidation reaction starting immediately. Reaction rate and product distribution were measured by oxygen consumption, HPLC, and NMR. The results showed 44.4% conversion with a selectivity to lactic acid of 92.4% The only by-product resulted from the further oxidation of lactic acid or hydroxyacetone to pyruvic acid 7.6%).

EXAMPLES 31 to 33

Hydroxypropanal was oxidized with molecular oxygen in a glass reactor equipped with a magnetic stirrer, gas distributor, and combined thermometer and pH sensor. The catalyst (0.7 g platinum on carbon, pretreated as described in J. Chem. Soc. Chem. Comm. 1995, 1377) hydroxypropanal (5.18 g, 88% pure, 61.6 mmol, remainder hydroxyacetone), and 70 g water were loaded into the reactor and heated to 60° C. under nitrogen, which was then replaced by oxygen flow. The pH was adjusted with 3.5M KOH or 1.75M $Na_2CO_3$, in the case of KOH by automatic titration. The results are shown in Table 6.

TABLE 6

| Example | pH, using | Time, hr | Conv % | Selectivity mol % | | | |
|---|---|---|---|---|---|---|---|
| | | | | LA | PA | AA | HA |
| 31 | 10, KOH | 3 | 100 | 74 | 7.6 | 3 | 15.4 |
| 32 | 8–9, $Na_2CO_3$ | 2.5 | 99 | 90 | 0.2 | 6 | 3.8 |
| 33* | 7.3, KOH | 3 | 93 | 79 | 0.2 | 0 | 15.6 |

*Other, unknown, species produced.
LA: lactic acid    AA: acetic acid
PA: pyruvic acid    HA: hydroxyacetone.

Steps (d) and (g)—Single stage Oxidative Hydrolysis of Hydroxyacetal to Lactic Acid

EXAMPLE 34

1.8 g of 2-hydroxy-1,1-dimethoxypropane were mixed with 10 g water, 0.2 g of a 5% platinum on carbon catalyst, and 0.1 g of an acidic ion exchange resin, Amberlyst 15, in a 30 ml flask equipped with stirrer, condenser, and gas inlet port. Oxygen at atmospheric pressure was passed through the reaction mixture for 23 hours at room temperature. Analysis showed 87% of the hydroxyacetal was converted, with molar selectivity of 30% to lactic acid, 68% to hydroxypropanal, and 0.5% to pyruvic acid.

Steps (d) and (i)—Hydrolysis to α-hydroxyaldehyde and ketone

EXAMPLES 35 to 48

Hydrolysis of Hydroxyacetal to 2-Hydroxypropanal and Hydroxyacetone

In these examples the effects of varying the reaction conditions on conversion and selectivities (given below in molar %) are observed. First, the effect of the molar ratio of water:substrate (hydroxyacetal) was investigated. The results are shown in Table 7.

TABLE 7

| | | Time, hours | | | | | | | | |
|---|---|---|---|---|---|---|---|---|---|---|
| | | 1 | 3 | 5 | 1 | 3 | 5 | 1 | 3 | 5 |
| Ex. No. | Molar ratio water:substrate | Conversion, % | | | OH-Propanal, % | | | OH-Acetone, % | | |
| 35 | 5:1 | 20 | 68 | 82 | 87 | 70 | 63 | 13 | 30 | 37 |
| 36 | 10:1 | 24 | 78 | 92 | 93 | 84 | 72 | 8 | 16 | 28 |
| 37 | 20:1 | 32 | 93 | 98 | 100 | 83 | 74 | 0 | 17 | 26 |
| 38 | 50:1 | 16 | 83 | 100 | 100 | 91 | 85 | 0 | 9 | 15 |

Reaction Conditions: Catalyst Concentration 5 wt %, H-β, Si:Al ratio 28:1. Temperature 70° C.

Second, the effect of varying the weight ratio of catalyst-:substrate was investigated. Results are shown in Table 8.

TABLE 8

| | | Time, hours | | | | | | | | |
|---|---|---|---|---|---|---|---|---|---|---|
| | | 1 | 3 | 5 | 1 | 3 | 5 | 1 | 3 | 5 |
| Ex. No. | Wt, %, catalyst to substrate | Conversion, % | | | OH-Propanal, % | | | OH-Acetone, % | | |
| 39 | 1 | 0 | 8 | 17 | — | 100 | 91 | — | 0 | 9 |
| 40 | 5 | 32 | 93 | 98 | 100 | 83 | 74 | 0 | 17 | 26 |

TABLE 8-continued

| Ex. No. | Wt, %, catalyst to substrate | Time, hours | | | | | | | | |
|---|---|---|---|---|---|---|---|---|---|---|
| | | Conversion, % | | | OH-Propanal, % | | | OH-Acetone, % | | |
| | | 1 | 3 | 5 | 1 | 3 | 5 | 1 | 3 | 5 |
| 41 | 10 | 56 | 97 | 99 | 93 | 70 | 56 | 7 | 30 | 44 |
| 42 | 20 | 96 | 99 | 100 | 78 | 41 | 23 | 22 | 59 | 77 |

Reaction Conditions: Molar Ratio Water:Substrate 20:1, Catalyst as in Example 26, Temperature 70° C.

Next, the effect of temperature was investigated. Results are as shown in Table 9.

TABLE 9

| Ex. No. | Temperature, ° C. | Time, hours | | | | | | | | |
|---|---|---|---|---|---|---|---|---|---|---|
| | | Conversion, % | | | OH-Propanal, % | | | OH-Acetone, % | | |
| | | 1 | 3 | 5 | 1 | 3 | 5 | 1 | 3 | 5 |
| 43 | 22 | 0 | 8 | 17 | — | 100 | 91 | — | 0 | 9 |
| 44 | 50 | 24 | 94 | 98 | 93 | 83 | 71 | 7 | 17 | 29 |
| 45 | 70 | 31 | 93 | 98 | 100 | 83 | 74 | 0 | 17 | 26 |
| 46 | 90 | 95 | 99 | 100 | 85 | 50 | 29 | 15 | 50 | 71 |

Conditions as in Example 31, but with variation of temperature.

The effect of changing the catalyst to ZSM-5, Si:Al ratio 30:1, under conditions similar to those of Example 46 was examined; the results are shown in Table 10.

TABLE 10

| Ex. No. | Catalyst | Time, hours | | | | | | | | |
|---|---|---|---|---|---|---|---|---|---|---|
| | | Conv, % | | | OH-Propanal, % | | | OH-Acetone, % | | |
| | | 1 | 3 | 5 | 1 | 3 | 5 | 1 | 3 | 5 |
| 47 | H-β | 95 | 99 | 100 | 85 | 50 | 29 | 15 | 50 | 71 |
| 48 | ZSM-5 | 17 | 54 | 100 | 53 | 46 | 32 | 47 | 54 | 68 |

The examples demonstrate that lactic acid may be produced in good yield or high selectivity, as desired.

What is claimed is:

1. A process for the manufacture of an α-hydroxy aldehyde or ketone in which the carbonyl group is protected which comprises (a) forming an acetal or ketal by reaction of an aldehyde or ketone and an alcohol or an ortho-ester, (b) decomposing the acetal or ketal to form a vinyl ether, and (c) oxidizing the vinyl ether in the presence of a carbonyl group-protective reagent to form the α-hydroxy aldehyde or ketone with the carbonyl group protected.

2. A process as claimed in claim 1, wherein the carbonyl group-protective reagent is an alcohol.

3. A process as claimed in claim 1, wherein step (a) is carried out in the presence of an acid catalyst.

4. A process as claimed in claim 1, wherein step (b) is carried out by pyrolysing the acetal or ketal.

5. A process as claimed in claim 1, wherein step (c) is carried out using a peracid.

6. A process as claimed in claim 5, wherein step (c) is carried out in the presence of a catalyst.

7. A process as claimed in claim 5, wherein step (c) is carried out in the presence of a Ti-containing molecular sieve.

8. A process as claimed in claim 1, wherein the protecting group is removed from an aldehyde or ketone by acid hydrolysis in the presence of a molecular sieve or ion-exchange resin in acid form.

9. A process as claimed in claim 8, which is carried out on an aldehyde, and the aldehyde is simultaneously or subsequently oxidized to an α-hydroxy acid using molecular oxygen, and in the presence of platinum.

10. A process for the manufacture of lactic acid which comprises forming an acetal by reaction of propanal and an alcohol, decomposing the acetal to form a propene ether, oxidizing the ether in the presence of an aldehyde group-protecting reagent to yield a protected 2-hydroxypropanal and removing the protection from the aldehyde group and oxidizing the resulting 2-hydroxypropanal to form lactic acid.

11. A process as claimed in claim 1, wherein a protected aldehyde is formed, and wherein the protected aldehyde is oxidized to an α-aldehydic acid.

12. A process as claimed in claim 8, wherein an unprotected aldehyde is formed and wherein it is rearranged to form an α-hydroxy ketone.

13. A process as claimed in claim 1, wherein a protected aldehyde is formed, and wherein it is oxidized to an α-keto acetal.

14. A process as claimed in claim 13, wherein the α-keto acetal is hydrolysed to α-keto aldehyde.

15. A process as claimed in claim 14, wherein the α-keto aldehyde is oxidized to an α-keto acid.

16. A process for the manufacture of an α-hydroxyketone which the carbonyl group is protected and isomerizing the resulting α-hydroxyaldehyde to an α-hydroxyketone, the process being carried out in the presence of an acid catalyst.

17. A process as claimed in claim 16, wherein the α-hydroxyaldehyde is 2-hydroxypropanal, and the isomerization is to hydroxyacetone.

18. A process as claimed in claim 16, wherein the catalyst is a zeolite.

19. A process as claimed in claim 16, wherein hydrolysis is carried out using a water:protected aldehyde molar ratio in the range of from 1:1 to 10:1.

20. A process as claimed in claim 16, carried out at a protected aldehyde:catalyst weight ratio of from 1:1 to 1000:1.

21. A process as claimed in claim 16, carried out at a temperature within the range of from 70 to 90° C.

22. A process as claimed in claim 1, wherein said carbonyl group-protective reagent is protic.

23. A process as claimed in claim 1, wherein said carbonyl group-protective reagent is selected from the group consisting of an alcohol, an acid, an amine, a thiol, and a combination thereof.

24. A process as claimed in claim 23, wherein said alcohol is a dihydroxy alcohol.

25. A process as claimed in claim 23, wherein said acid is a carboxylic acid.

* * * * *